US012123251B2

(12) United States Patent
Benkreira et al.

(10) Patent No.: US 12,123,251 B2
(45) Date of Patent: *Oct. 22, 2024

(54) DEPLOYABLE BANK SECURITY SYSTEM

(71) Applicant: Capital One Services, LLC, McLean, VA (US)

(72) Inventors: Abdelkader Benkreira, Washington, DC (US); Daniel Marsch, Arlington, VA (US); Joshua Edwards, Philadelphia, PA (US); Michael Mossoba, Arlington, VA (US)

(73) Assignee: CAPITAL ONE SERVICES, LLC, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/202,658

(22) Filed: May 26, 2023

(65) Prior Publication Data

US 2024/0076928 A1 Mar. 7, 2024

Related U.S. Application Data

(63) Continuation of application No. 17/359,216, filed on Jun. 25, 2021, now Pat. No. 11,697,961, which is a continuation of application No. 16/683,133, filed on Nov. 13, 2019, now Pat. No. 10,735,198.

(51) Int. Cl.
*E05G 7/00* (2006.01)
*E05G 5/00* (2006.01)
*F41H 5/013* (2006.01)
*F41H 5/04* (2006.01)
*F41H 5/24* (2006.01)
*G06N 20/00* (2019.01)
*H04L 9/32* (2006.01)
*H04L 9/40* (2022.01)

(52) U.S. Cl.
CPC ............ *E05G 7/004* (2013.01); *E05G 5/006* (2013.01); *F41H 5/013* (2013.01); *F41H 5/0492* (2013.01); *F41H 5/24* (2013.01); *G06N 20/00* (2019.01); *H04L 9/3234* (2013.01); *H04L 63/06* (2013.01); *H04L 63/083* (2013.01); *H04L 63/102* (2013.01)

(58) Field of Classification Search
CPC .. E05G 5/00; E05G 5/006; E05G 5/02; E05G 7/00; E05G 7/002; E05G 7/004; F41H 5/013; F41H 5/04; F41H 5/0492; F41H 5/0478; F41H 5/24
See application file for complete search history.

(56) References Cited

U.S. PATENT DOCUMENTS

| | | |
|---|---|---|
| 1,247,579 A | 11/1917 | Sears |
| 1,284,790 A | 11/1918 | Schafer |
| 1,915,698 A | 6/1933 | Rohrig |
| 1,879,427 A | 9/1949 | Mathew et al. |
| 2,984,194 A | 5/1961 | Jennings |

(Continued)

FOREIGN PATENT DOCUMENTS

| | | |
|---|---|---|
| GB | 2339588 | 2/2000 |
| GB | 2379715 | 3/2003 |

*Primary Examiner* — Christopher J Boswell
(74) *Attorney, Agent, or Firm* — HUNTON ANDREWS KURTH LLP

(57) ABSTRACT

Embodiments of systems, methods, and devices for protecting service personnel by deploying a physical barrier are described. Further embodiments describe additional security features such as lights, sirens, cameras, electronic locks, timers, and/or notifying security personnel or local law enforcement when the system is activated.

20 Claims, 12 Drawing Sheets

(56) References Cited

U.S. PATENT DOCUMENTS

| | | |
|---|---|---|
| 3,148,640 A | 9/1964 | Nadina |
| 3,230,912 A | 1/1966 | Hohmann |
| 4,034,685 A | 7/1977 | Word |
| 4,372,225 A | 2/1983 | Tissot et al. |
| 4,748,914 A | 6/1988 | Cardinal |
| 5,534,343 A | 7/1996 | Landi et al. |
| 5,636,579 A | 6/1997 | Shelley |
| 5,655,461 A | 8/1997 | Gilbert |
| 5,860,371 A | 1/1999 | Shelley |
| 6,019,389 A | 2/2000 | Burgi et al. |
| 6,997,218 B1 | 2/2006 | Garcia et al. |
| 7,216,576 B2 | 5/2007 | Henry et al. |
| 7,921,759 B2 | 4/2011 | Warren |
| 7,931,297 B2 | 4/2011 | Abe et al. |
| 8,272,311 B2 | 9/2012 | Cannon |
| 9,170,071 B2 | 10/2015 | Howland |
| 9,797,182 B2 | 10/2017 | Raap et al. |
| 10,739,113 B1 | 8/2020 | Bosen et al. |
| 11,072,967 B2 | 7/2021 | Benkreira et al. |
| 2005/0029148 A1 | 2/2005 | Rust |
| 2005/0053769 A1 | 3/2005 | Imblum et al. |
| 2008/0178781 A1 | 7/2008 | Kim |
| 2012/0186425 A1 | 7/2012 | Kocher et al. |
| 2015/0082976 A1 | 3/2015 | Meldner et al. |
| 2015/0233678 A1 | 8/2015 | Smith |
| 2016/0209181 A1 | 7/2016 | Adrain |
| 2017/0102214 A1 | 4/2017 | Wright et al. |
| 2017/0102216 A1 | 4/2017 | Lam |
| 2019/0383346 A1 | 12/2019 | Clayton |
| 2022/0196370 A1 | 6/2022 | Milo et al. |

DEPLOYABLE BANK SECURITY SYSTEM

CROSS-REFERENCE TO RELATED APPLICATIONS

This application is a continuation of U.S. patent application Ser. No. 17/359,216 filed Jun. 25, 2021, which is a continuation of U.S. patent application Ser. No. 16/502,777 filed Jul. 3, 2019, now U.S. Pat. No. 11,072,967, the complete disclosures of which are incorporated herein by reference in their entireties.

FIELD OF THE INVENTION

This disclosure relates to the protection of public-facing service personnel, and more specifically, to systems and methods for protecting service personnel, cashiers, or other personnel who handle valuable goods from robbery.

BACKGROUND

Bank service personnel, cashiers, and other customer-facing service personnel who handle valuable materials are often in close proximity to the customers or other individuals with which they interact, placing them at risk of a robbery or other criminal activity. Existing security devices typically create a physical barrier between the service personnel and the customer, allowing items to be passed through a small opening or drawer. These devices can create an unwelcoming atmosphere and often interfere with the routine activity of most service personnel.

In addition to being physically cumbersome, existing security devices can interfere with relationship building and providing high-quality customer service. Forcing customers to speak through an intercom or vent holes in a physical barrier can create an uncomfortable environment, slow the conduct of business transactions, and reduce any opportunity for relationship building between the customer and service personnel. This can lead to diminished or lost business, as the customer may feel more welcome at an institution which does not employ permanent physical barriers.

Existing physical barriers can appear unsightly and can convey an impression of danger as it appears the institution anticipates routine criminal activity in its retail locations and lacks other, less intrusive means of stopping such activity. This can lead customers to feel uncomfortable and generally unwelcome, causing them to transact their business elsewhere. The potential cost of this lost business can be significant. Due to these and other drawbacks associated with permanent physical barrier security devices, many institutions do not provide any physical security devices for the protection of service personnel or cashiers in the event of a robbery. This leaves service personnel at risk in the event of a robbery, and an armed robbery in particular. Therefore, a need exists for a rapidly deployable physical barrier security system which may be stored inconspicuously and deployed quickly to create a physical barrier, separating service personnel from a potential robber or other assailant.

SUMMARY

Therefore, it is an object of this disclosure to describe systems and methods for deploying physical security devices. Each of these inventions seeks to create a physical barrier, separating service personnel from a potential robber or assailant, thereby protecting the service personnel from potential harm and preventing the potential robber from obtaining valuable items.

Embodiments of the present disclosure provide a panel, preferably a bullet resistant panel may be rapidly deployed when an activation switch is pressed. In some of these embodiments, the panel is stored in a discrete location, such as within a desk or counter, and is moved into position using a deployment mechanism such as an actuator or actuation cylinder with a source of pressurized fluid when the deployment mechanism receives a signal from the activation switch. In some of these embodiments, the panel is guided by a track which may be embedded into a service personnel station. This allows the panel to be moved rapidly and reliably into position when the service personnel presses an activation switch. Certain embodiments use two, or more than two panels which are each deployed when the service personnel presses the activation switch. Using multiple panels may help to separate the service personnel and the assailant more quickly as the two panels can be closed simultaneously from opposite directions, reducing the total distance each panel has to travel in order to create a physical barrier. In some embodiments, these two panels will interlock or latch together in order to avoid creating a weak point in the barrier.

In some embodiments, the barrier may be a flexible barrier which is rapidly inflated in order to separate the service personnel and the potential assailant. In these embodiments, the barrier is preferably a bullet and/or knife resistant material. In order to inflate the barrier quickly a source of compressed air may be used or a pyrotechnic material similar to those used when deploying air-bags.

In some embodiments, the inflatable barrier may additionally or alternatively be filled with an expanding foam. In certain embodiments, the expanding foam will harden or cure rapidly, resulting in a solid physical barrier. The inflatable barrier may be significantly thicker than the panel as the inflatable barrier can be stored inconspicuously when it is deflated, but be very large when inflated.

In other embodiments, the physical barrier can be built into a service personnel booth directly. Service personnel booths or desks often have a customer service window which is created by a counter or desk surface, two vertical members and an upper cross member. In these embodiments, a track may be place in the two vertical members in order to guide a shield or other physical barrier rapidly into position when an initiation button is pressed.

Any or all of the above embodiments may also be combined with additional security features when the physical barrier is deployed. The various systems may be designed to activate security lights, sirens, cameras, electronic locks, timers, and/or notify security personnel or local law enforcement when the system is activated. Certain embodiments may also utilize dye packs, or dye sprays in order to mark the potential assailant for later identification when the system is activated.

In order to avoid accidentally activating a system, certain embodiments will require a two-finger press, pressing multiple buttons simultaneously, pressing a button multiple times in order to activate the system.

It will be understood that, while the disclosed inventions are typically referred to in the context of service personnel, these systems and methods may be utilized to protect a wide range of personnel including, but not limited to, cashiers, sales people, jewelers, vendors, customer service personnel, retailers, public safety personnel such as police officers or hospital intake personnel, or any other individual who interacts with customers, clients, or other members of the public.

It is to be understood that both the foregoing general description and the following detailed description are exemplary and explanatory only, and are not restrictive of the disclosed embodiments.

DETAILED DESCRIPTION OF EXAMPLE EMBODIMENTS

The present disclosure provides systems, methods, and devices for the protection of personnel from harm and/or robbery. Embodiments described herein utilize a movable physical barrier which can be stored inconspicuously, allowing for normal business operations, and rapidly deployed when necessary. The disclosed movable security device allows for normal business activity to take place without the impediments of permanent, fixed, or otherwise obtrusive security devices which may make customers or clients feel uncomfortable or unwelcome. Some embodiments of the disclosed security devices are also bullet resistant and may be used to stop or deter an armed assailant.

Figure 1A:
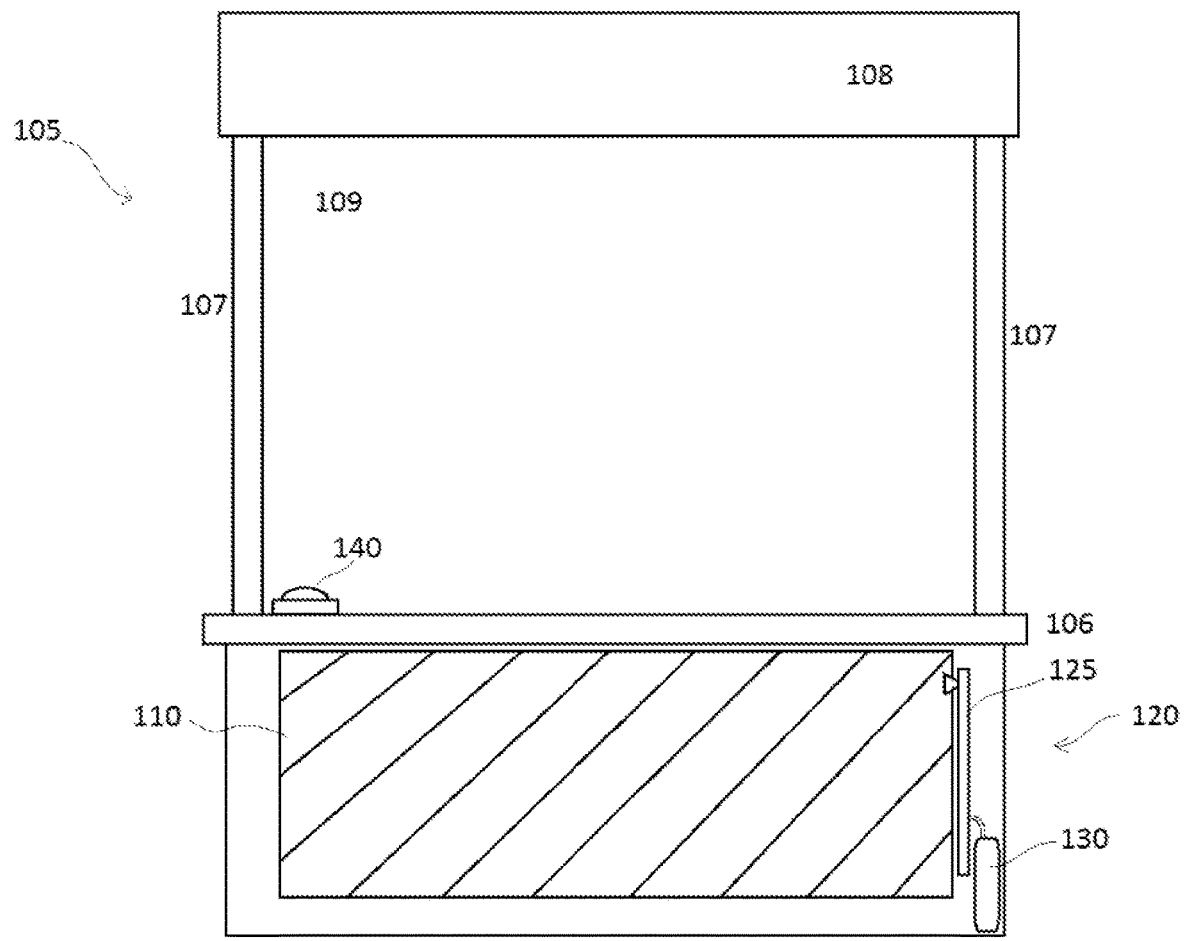
FIG. 1A illustrates a security system having a panel in the stored position according to an example embodiment.
Figure 1B:
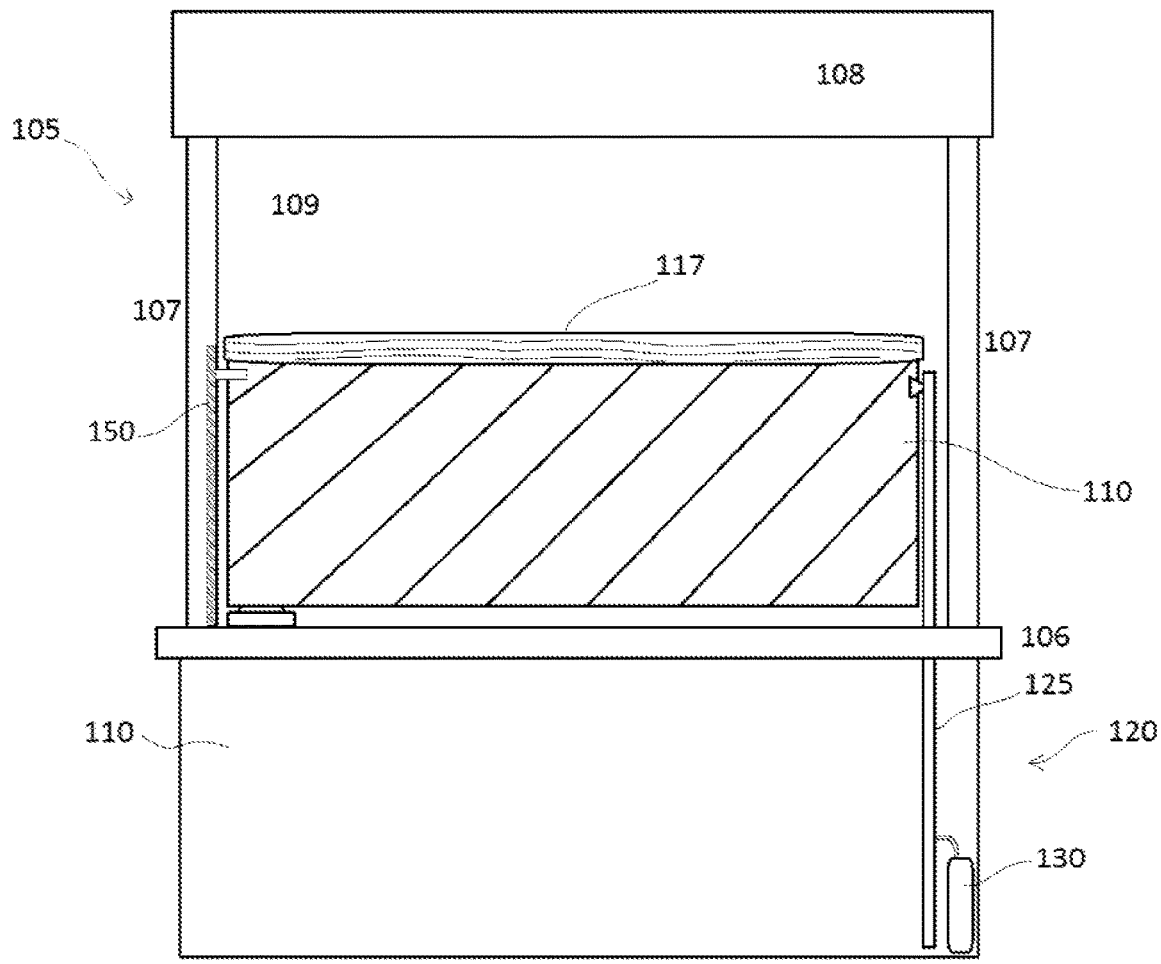
FIG. 1B illustrates a security system using a panel with a bumper in the deployed position according to an example embodiment.

FIG. 1A depicts one potential embodiment of the disclosed system in which a bullet resistant panel 110 may be stored underneath a counter 106 or desk top where service personnel or other customer facing personnel work. The panel 110 may remain in its stored position for an extended period of time. When in stored position, the panel 110 may not be visible to, or maybe largely hidden from, customers standing on the opposite side of the counter 106 from the service personnel. An activation switch 140 may be discretely positioned near the service personnel so that it may be pressed quickly and potentially covertly in the event a service personnel is confronted by a robber or assailant. The panel 110 can be connected to an actuator 125. When the service personnel presses the activation switch 140, the activation switch 140 generates a signal, the actuator 125, upon receiving the signal moves the panel 110 from the stored position to the deployed position as shown in FIG. 1B. In the deployed position, the panel 110 creates a physical barrier between the service personnel and potential assailant. In an embodiment, the barrier can be complete, preventing the assailant from gaining access to the service personnel and/or other personnel. In some embodiments, the barrier only prevents direct access from the assailant to the service personnel but it may be possible to circumvent the panel by going around, over, or under the deployed panel.

Figure 2A:
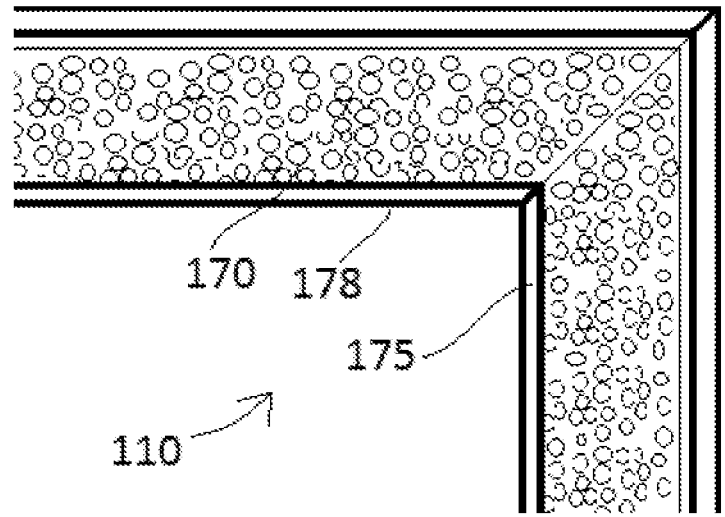
FIG. 2A illustrates a cutaway view of the interior of a panel including a shell, liner, and filler material according to an example embodiment.
Figure 2B:
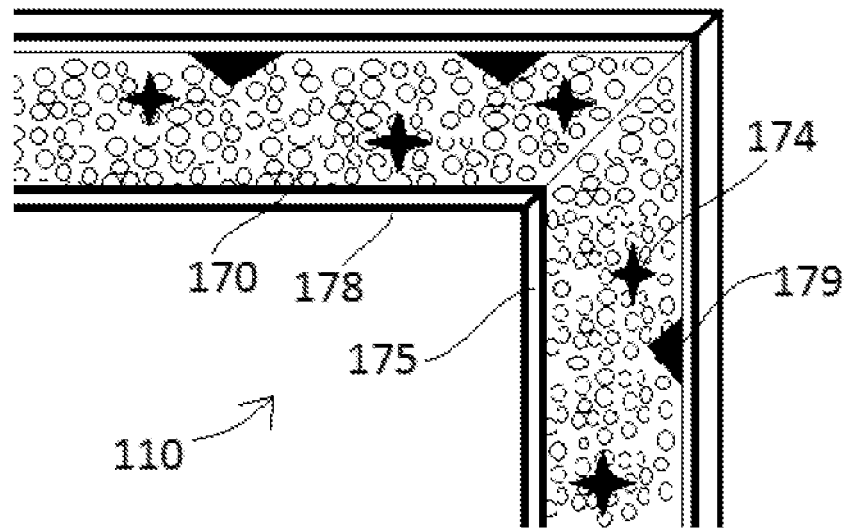
FIG. 2B illustrates a cutaway view of the interior of a panel including a shell, liner, filler material and internal structures and geometric shapes designed to dissipate force according to an example embodiment.

The panel 110 is preferably bullet and/or knife resistant but may be made of a wide range of materials including, but not limited to, glass, Kevlar, polycarbonate, polyethylene, Lexan, carbon fiber composites, wood, rubber, elastomers, polymers, foams, beads, ceramics, steel, titanium, metal alloys and/or combinations thereof. In an embodiment, these materials may have bullet resistance, shatter resistance, visibility reducing, or other protective properties. The panel 110 may be solid, hollow, or a composite of multiple materials. In an embodiment, the panel 110 will be made of a ridged shell 178 with the internal volume filled with a secondary filler material 170 as shown in FIG. 2. In an embodiment, the interior volume of the panel can be filled with impact absorbing particles. Accordingly, the panel may be self-healing and able to absorb additional gun shots or other physical trauma as the impact absorbing particles will collapse and fill any void created by a gun shot. This prevents or reduces the weakening of the panel due to multiple gun shots in close proximity to each other. The panel may include an inner liner 175 of rubber or elastomer designed to substantially close around any opening or damage to the panel in order to prevent the impact absorbing particles from falling out of the outer shell. This configuration may allow the panel to be relatively light weight compared to a solid metal panel of equivalent dimensions. The panel may contain various internal geometries 174 and structures 179 designed to dissipate the force of a gun-shot across a wider area and/or in multiple directions.

In an embodiment, when the panel 110 can be in the deployed position and protruding vertically from the counter 106, the panel 110 will be oriented at a specified angle from the vertical. For example, the panel 110 may be angled at least about 5 degrees from vertical, at least about 15 degrees from vertical, at least about 25 degrees from vertical, at least about 35 degrees from vertical, or at least about 45 degrees from vertical. The panel 110 may be angled either towards forwards towards the potential assailant or backwards towards the service personnel. It is understood that the panel 110 may be angled as necessary to fit the current environment and the likely threats that are encountered.

It is further understood that the panel 110 may vary in length, height, thickness, and material, and with each of these affecting the weight of panel 110. In turn, the weight of a panel 110 informs other details of the system design. For example, a heavier panel 110 may require additional actuators 125 when compared to a lighter weight panel 110. A lighter weight panel 110 may be able to be accelerated and decelerated more quickly, thereby resulting in a faster deployment when compared to a heavier panel 110. A heavier panel 110 may require a higher pressure pressurized fluid source 130 to drive the associated actuator 125 and may require an additional deceleration mechanism in order to stop the movement of the panel 110 once it is in position without damaging the system as a whole.

In an embodiment, the dimensions of a panel 110 may inform other details of the system. For example, a panel 110 which is thinner may be less resistant to penetration or may need to be made of a more resilient material as compared to a thicker panel 110. A thicker panel 110 may include sufficient volume for lighter weight and/or more cost effective materials to provide an acceptable degree of protection. In some embodiments, the panel 110 will be at least about six inches thick, at least about 12 inches thick, at least about 18 inches thick, at least about 24 inches thick, or at least about 36 inches thick.

Each of these considerations will be readily understood by one of ordinary skill and will inform the specific configuration of the system and selection of materials and components depending on the precise conditions in which the system is utilized.

In an embodiment, multiple service personnel booths 105 are each equipped with the disclosed security system and can be operatively connected together. Each booth 105 may be configured to have a panel 110 stored underneath a counter 106 and an activation switch 140. When service personnel presses any of the activation switches 140, the system can be designed to deploy all of the panels 110 or a portion of the panels 110. The system may be designed to deploy the panel 110 at the booth 105 where the activation switch 140 was pressed and the panel 110 at each adjacent booth 105 or at a series of adjacent booths 105. In this manner, most or all service person who may be in proximity to a potential assailant may be protected without being required to individually press an activation switch 140. This also has the benefit of deploying a panel 110 in a booth 105 where service personnel may not be present.

Figure 3:
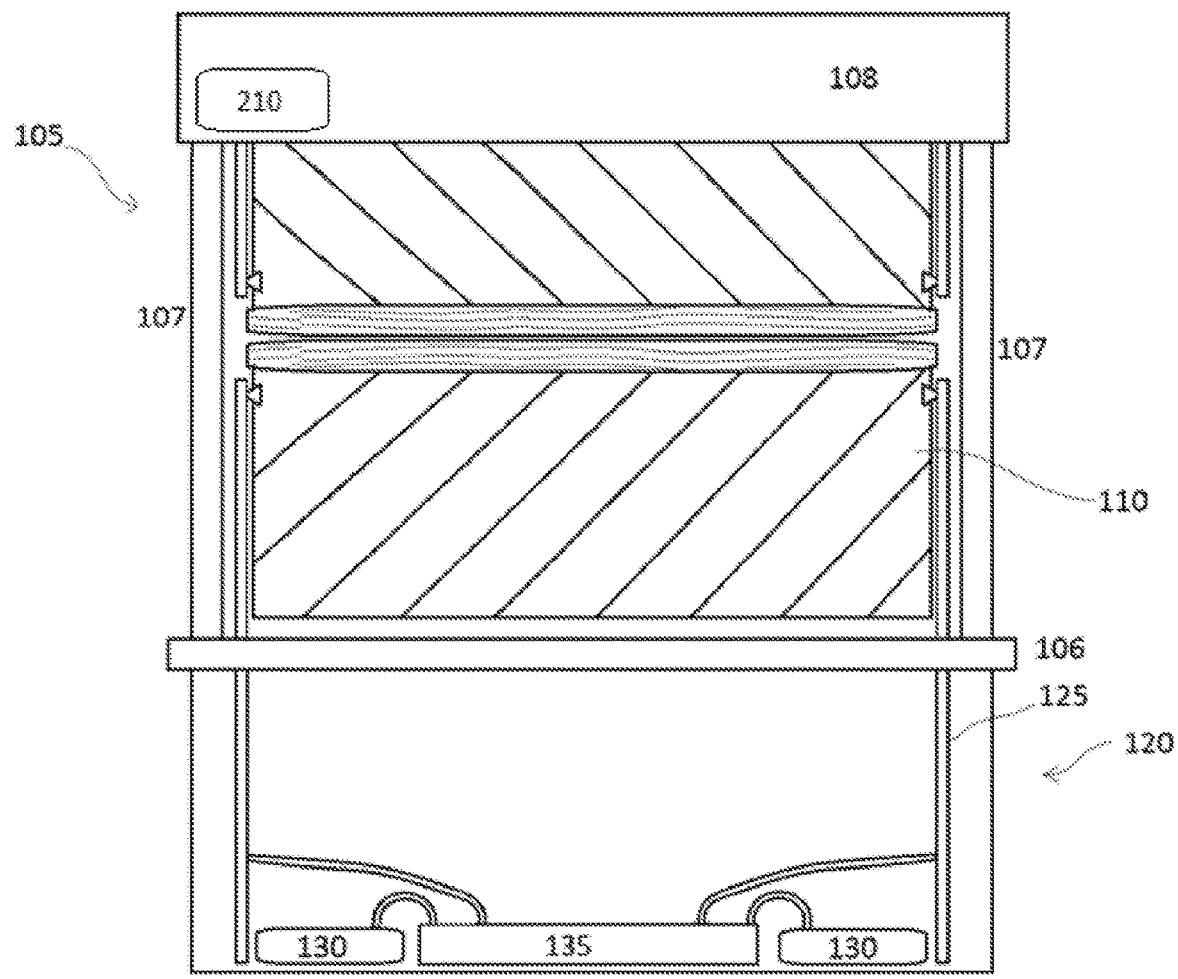
FIG. 3 illustrates two panels closing in opposite directions and multiple actuators powered with multiple sources of pressurized fluid plumbed through a manifold according to an example embodiment.

The actuator 125 may be, but is not limited to being, an actuation cylinder, electronic actuator, electro-magnetic actuator, hydraulic piston, pneumatic cylinder, or electric motor assembly. In some embodiments, the actuator 125 can be an actuation cylinder which can be connected to a source of pressurized fluid 130 such as air or hydraulic fluid. In these embodiments, when the activation switch 140 is pressed and a signal is generated, the pressurized fluid causes the actuator 125 to respond by extending and moving the panel 110 from the stored position to the deployed position. In such embodiments, the source of pressurized fluid 130 may be located locally or may be located remotely and fluidly connected to the actuator 125 using pipes, tubes, and/or pressurized lines. The source of pressurized fluid may be, but is not limited to, a pressurized tank of air, nitrogen, carbon dioxide, or other gas which may be connected to an actuator 125. The source of pressurized fluid may also be, but is not limited to, a source of pressurized liquid, such as hydraulic fluid. In certain embodiments, multiple actuators 125 will be used for each panel 110. In such embodiments, a single source of pressurized fluid 130 may be connected to all of the actuators 125, or individual sources of pressurized fluid 140 may be connected to each actuator 125 individually. Further, as shown in FIG. 3, multiple sources of pressurized fluid 130 will be connected to each actuator 125 through a manifold 135. This redundancy may be implemented as a safety feature, i.e., if one source of pressurized fluid 130 fails, the actuators 125 will still be activated and will deploy the panel 110, as a method of deploying large or heavy panel 110, or to facilitate the use of smaller, less obtrusive sources of pressurized fluids.

In many customer service locations, each service personnel works at a separate area designated by an individual service personnel window 109. These windows may be any size, and are often quite large, but are typically defined by a counter or desk surface 106 at the bottom, two vertical members 107, and an upper cross member 108. In some locations, there may only be one service personnel window 109, while in others there may be several windows 109 in a line or located throughout a store or other establishment. In some embodiments, the panel 110 will be connected to a guide track 150, which may be mounted to the vertical members 107 of the window 109. In a preferred embodiment, each vertical member 107 will include a guide track 150 and the tracks 150 will be arranged such that the panel 110 occupies substantially all of the window 109 when it is deployed. In these embodiments, the rapid deployment of the panel 110 blocks substantially all access to the service personnel, giving the service personnel time to escape, hide, take additional security measures, or notify law enforcement.

In an embodiment, the guide track 150 is a linear track which may be secured to the vertical members 107 of the window 109. The guide track 150 may be preferably between approximately 0.5 and 4 inches wide and approximately between 3 and 5 feet long, however, it is understood that the dimensions for the track may be determined by the dimensions of the panel 110 and the guidance necessary for deployment and retraction.

The guide track 150 may be rectangular or ellipsoid, and can be significantly longer than it is wide. The guide track 150 may be recessed into the vertical members 107 or may protrude from the vertical member slightly into the window 109.

The guide track 150 may be oriented vertically or its orientation can be angled from the vertical. For example, the orientation of the guide track 150 can range from approximately 5 degrees from vertical to approximately 45 degrees from vertical. The guide track 150 may be angled either forwards towards the potential assailant or backwards towards the service personnel. It is understood that the guide track 150 may be angled as necessary to fit the surrounding environment and the likely threats that are encountered.

It is understood that the guide track 150 may be modified to accommodate the needs of the panel 110 and/or barrier 310 and the anticipated deployment conditions.

As shown in FIG. 3, more than one panel 110 may be used. In an embodiment, each panel 110 operates substantially described in a single panel embodiment, but the panels 110 may be arranged such that they occupy the space between the service personnel and the assailant more quickly when multiple panels 110 are deployed. In an embodiment, a second panel 110 can be stored above the service personnel window 109 and moved down by the actuator 125 when the activation switch 140 is pressed. The second panel 110 may be lowered at the same, or substantially the same time as the first panel 110 is raised. This allows the window 109 to be fully occupied by the panels 110 while only requiring each panel 110 to travel a fraction of the distance needed to occupy the entire window 109. The speed of deployment can be a significant consideration for security purposes. By reducing the total distance each panel 110 must travel, the time required to fully block the window 109 can also be reduced.

When a panel 110 is deployed, it will be rapidly moved from the stored position to the deployed position. In an effort to avoid injury to anyone who may be in the path of the panel 110 as it is moving, some embodiments include a bumper 117 on the edge of the panel 110. The bumper 117 is typically made of soft or flexible material which can be designed to cushion the impact of the panel against an individual's arm or other body part. In some embodiments, the bumper 117 will force any object in the path of the panel 110 to be moved out of the way as the panel 110 is moved into the deployed position. In some embodiments, the bumper 117 may be sufficiently thick that objects and/or body parts may become trapped, but not significantly harmed, if they are in the path of the panel 110 or panels as they are deployed. In embodiments which utilized two or more panels 110, the bumpers 117 on opposing panels may be formed to allow the panels and bumpers to overlap and/or interlock when the panels 110 are deployed. The bumpers 117 may be made of material including, but not limited to foams, rubbers, elastomers, silicone, inflatable materials, mesh, screen, fabrics, and combinations thereof.

When the service personnel presses the activation switch 140, thereby generating a signal, multiple additional security measures may be activated in addition to deploying a security panel. In certain embodiments, the activation switch may be operably connected to a camera system 210 such that pressing the activation switch causes camera system 210 to start recording, maintain recorded images which may have otherwise been deleted, and/or focus on the area surrounding the service personnel who pressed the activation switch 140. Camera system 210 may include one or more cameras at one or more locations. Additional security measures which are activated upon receiving a signal may include, but are not limited to activating security alarms, sirens, flashing lights both inside and outside the building, electronic locks on doors and safes, timers which prevent the opening of drawers, doors, cabinets, or safes for a predetermined time period, sprinkler systems, and/or notifying law enforcement or other security personnel.

In order to avoid inadvertently deploying the security panels 110, the activation switch 140 may be designed to require more than a single press in order to generate a signal. In some embodiments, the activation switch 140 will require a two-finger press in order to generate a signal. Other potential requirements include, but are not limited to, pressing the activation switch a pre-determined number of times, in a pre-determined rhythm, and/or for a pre-determined amount of time. Still more potential requirements include pressing more than one activation switch 140 simultaneously or in a pre-determined sequence, opening a cover and then pressing the activation switch 140, pressing the switch 140 with a predetermined amount of force or any combination thereof.

If multiple activation switches 140 are required, the switches may be placed adjacent to each other in order to facilitate easily activating generating a signal, or may be placed remotely from each other in order to guard against accidentally generating a signal. Remotely located buttons may be placed on different sides of a service personnel station or may be placed at different elevations on the same side of a service personnel station. One of the activation buttons 140 may be placed at about floor level and/or be configured to be pressed with the service personnel's foot. In an embodiment, generating a signal may require the use of a key in addition to, or alternatively to pressing an activation switch 140.

In an embodiment, an activation switch 140 may be located away from the counter 106 where the service personnel works. An activation switch 140 may be placed on the wall behind the service personnel station, near a remotely located security personnel station, in a back office, inside a drawer or cabinet, underneath the counter 106, or any other location which allows the activation switch 140 to be pressed in the event of a robbery or perceived threat.

In an embodiment, the activation switch 140 may also be configured to function as a safety switch or global shut-off to be used for maintenance purposes. In some embodiments, if multiple switches 140 are pressed simultaneously, the system may be deactivated for a predetermined period of time, or until the system is reactivated. In some embodiments, multiple switches, 140, multiple remotely located switches 140, or substantially all activation switches 140 may be required to be pressed within a given time frame, or simultaneously, or pressed and held down for a predetermined period of time in order to deactivate the system. Once the system is deactivated, it may be safer to perform maintenance functions or other necessary tasks without potentially deploying the system.

In an embodiment, the security panels 110 and the activation switch 140 may be incorporated into an electronic monitoring system, and may be automatically triggered based on light, sound, vibration, or motion detectors. This may allow for remote or overnight monitoring of a sensitive location, and convey the benefits of panel deployment even in the absence of any security personnel.

Figure 4:
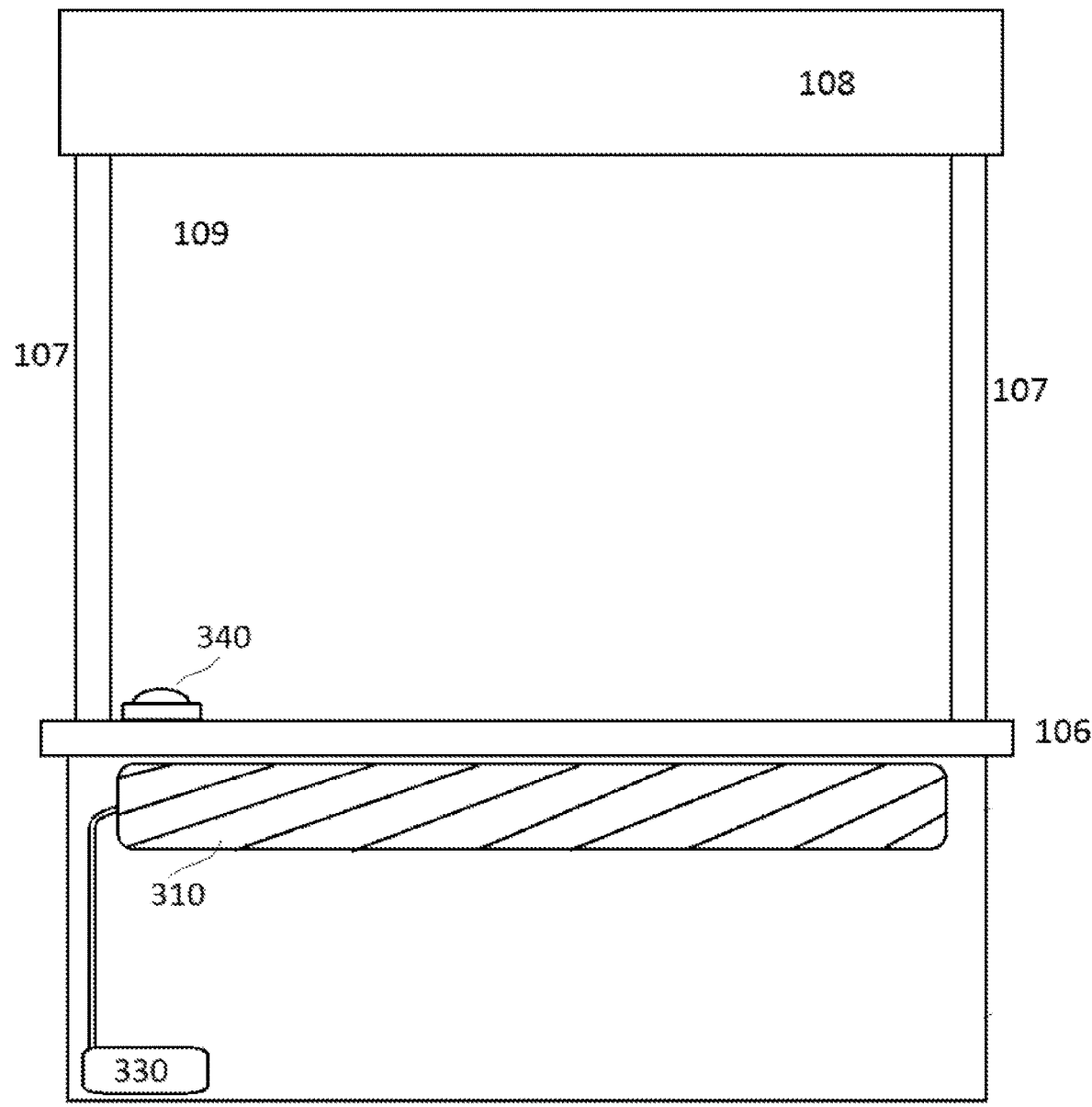
FIG. 4 illustrates the security system utilizing an inflatable barrier in the stored position according to an example embodiment.

Other embodiments of the disclosed systems includes an inflatable barrier 310 rather than or in addition to a panel 110. In these embodiments, when the service personnel presses an activation button 340, the activation button 340 sends a signal to an inflation fluid source 330. The inflation fluid source 330, upon receiving the signal, directs inflation fluid into the inflatable barrier 310, thereby causing the previously stored and deflated barrier 310 to expand and form a physical barrier separating the service personnel and a potential assailant. In many embodiments, the inflatable barrier 310 can be made of bullet and/or knife resistant material. FIG. 4 depicts a service personnel station with an inflatable barrier 310 folded in the stored position.

Figure 5:
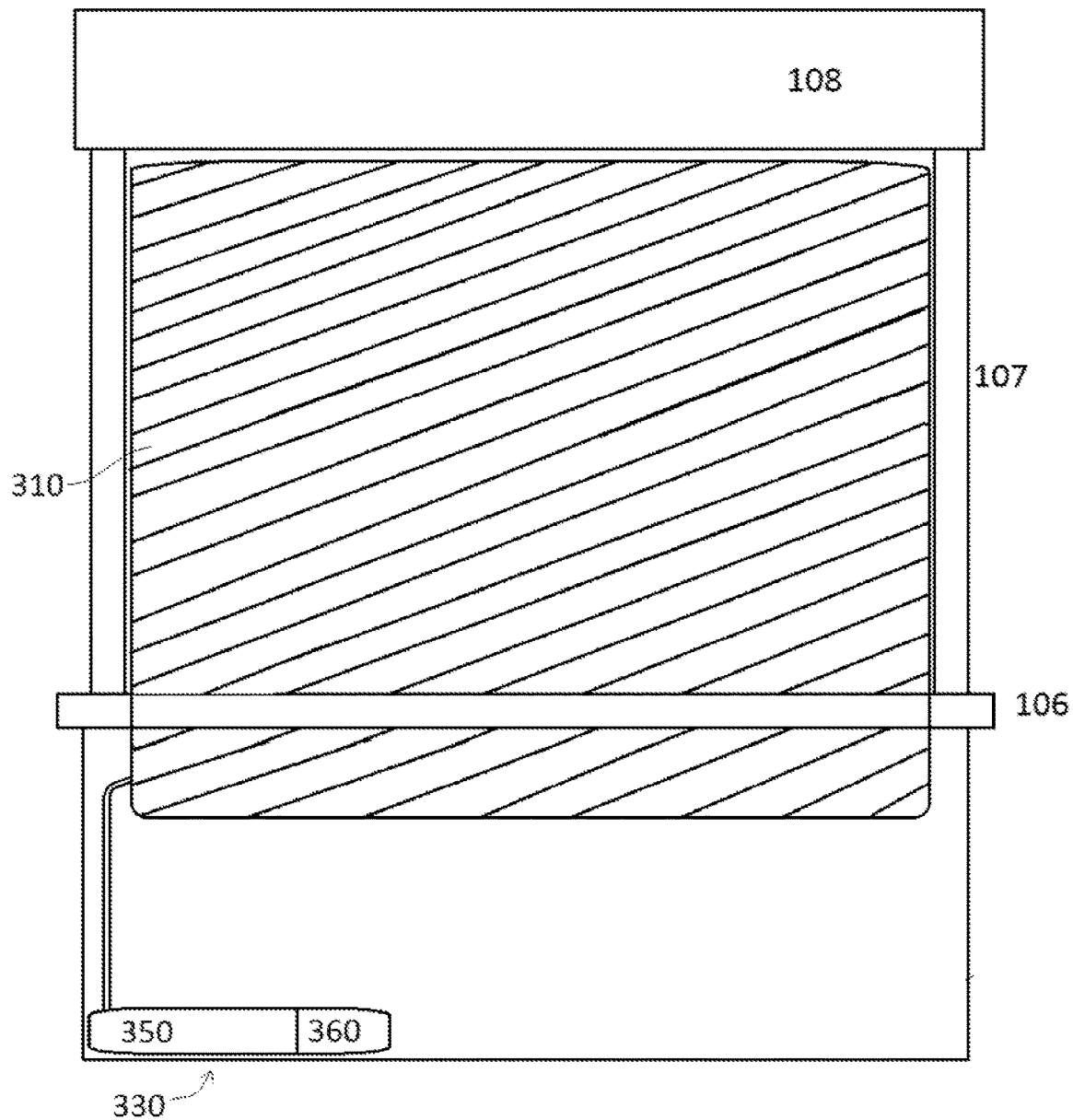
FIG. 5 illustrates a security system utilizing an inflatable barrier in the deployed position according to an example embodiment.

The source 330 of inflation fluid may include, but is not limited to, a tank of compressed gas or expanding foam which may be used to rapidly inflate the barrier, pyrotechnic materials 350 which may be ignited in order to produce a volume of inflation fluid, and/or chemical materials which generate an inflation fluid when reacted with another chemical, heat, electricity, and/or oxygen. In some embodiments, an energizable ignitor 360 will be activated when the activation button is pressed and used to ignite the pyrotechnic material. FIG. 5 depicts an embodiment in which pyrotechnic materials 350 are ignited using an energizable ignitor 360 in order to produce inflation fluid directed to the inflatable barrier 310 with the inflatable barrier 310 in the deployed position.

In certain embodiments, the system includes a filler material 170 which can be driven into the interior of the inflatable barrier as it is being inflated. The filler material 170 may be an expanding material itself, such as an expanding foam or polymer, or may be a solid material, or may be a liquid material that is delivered into the interior of the inflatable barrier 310. The filler material 170 may help the barrier 310 to maintain its size and/or shape after being attacked, punctured, or shot. Filler material 170 may include, but is not limited to foam, sand, beads, particles, ceramics, glass, latex, rubber, elastomers, saw dust, wood, polymers, Styrofoam, geometric shapes, and/or combinations thereof. The filler material 170 may be used to create a wider barrier between the service personnel and the potential assailant.

In an embodiment, the interior volume of the barrier may contain impact absorbing beads or particles. The panel may be substantially self-healing and able to absorb additional gun shots as the impact absorbing particles will disperse and fill any void potentially created by a gun shot. This prevents or reduces the weakening of the barrier due to multiple gun shots in close proximity to each other.

In an embodiment, a container of filler material 170 will be connected to the inflatable barrier 310 and configured to direct filler material into the inflatable barrier 310. The container itself may be pressurized, or may be connected to a source of pressurized fluid which may be used to help transport the filler material from the container into the inflatable barrier.

In an embodiment, the inflatable barrier 310 will be lined with a self-healing liner 175 which can be designed to reduce or substantially seal any opening in the inflatable barrier in the event the barrier material is punctured. This may assist with keeping the barrier 310 inflated and/or retaining the filler material 170 within the barrier 310 in the event the barrier 310 is punctured.

Figure 6:
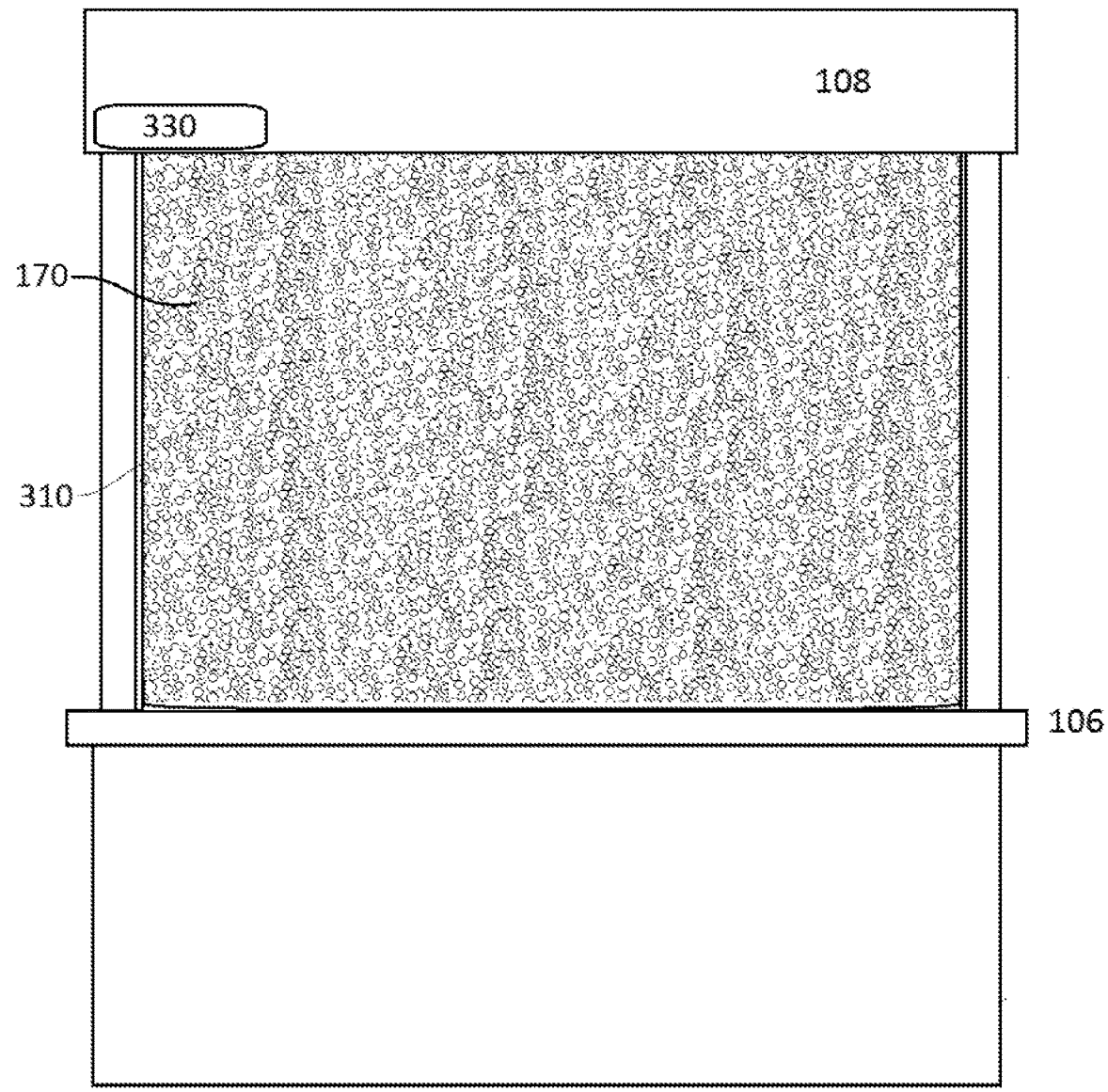
FIG. 6 illustrates a security system utilizing an inflatable barrier mounted above the service personnel window in the deployed position and filled with filler material according to an example embodiment.

In an embodiment, the inflatable barrier 310 will be stored above the area in which the service personnel interacts with customers and any potential assailant. In these embodiments, as shown in FIG. 6, when the barrier 310 is inflated, the barrier 310 will rapidly expand downwards. As the barrier 310 expands downward, filler material 170 may be directed to the interior of the barrier 310 from above. Because the filler material 170 can be added from above, into the sealed inflatable barrier 310, the filler material 170 will come to rest in the inflatable barrier 310, creating a substantial physical barrier and requiring less energy in order to transfer filler material 170 into the inflatable barrier 310 than raising the filler material 170 from below.

Figure 7:
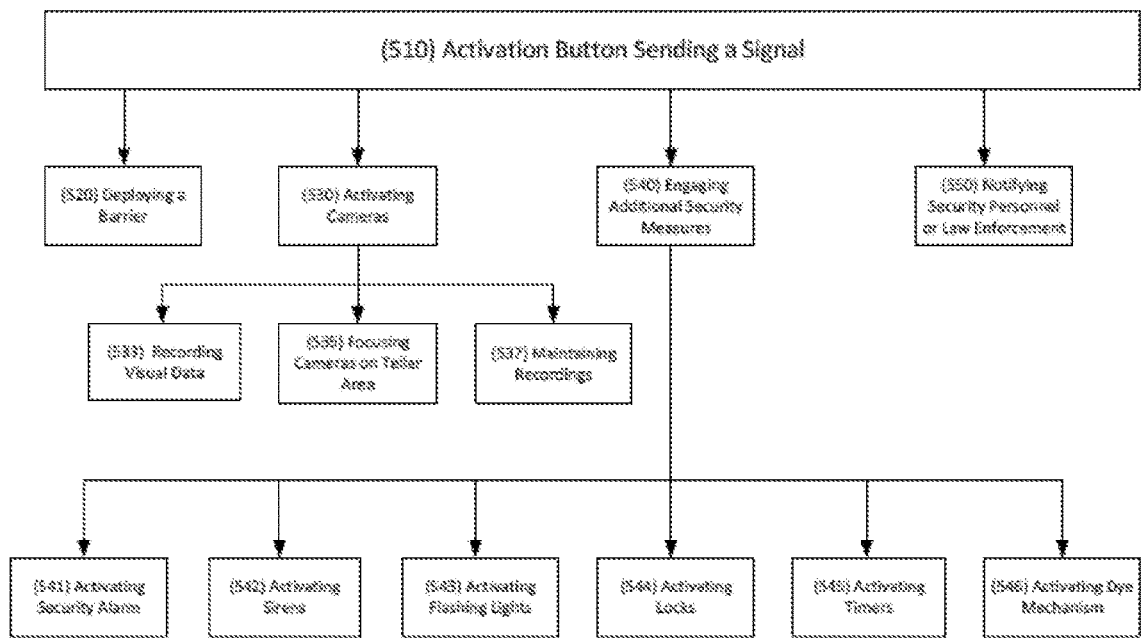
FIG. 7 illustrates a method for operating an activated security system according to an example embodiment.

As discussed above any additional security measures may be engaged with all of the embodiments described herein. In some embodiments, when the service personnel presses the activation button 340, the activation button 340 may activate a camera system 210 and cause cameras to start recording, maintain recorded images, and/or focus on the area surrounding the service personnel. Additional security measures may also include, but are not limited to activating security alarms, sirens, flashing lights inside or outside of the building, electronic locks on doors and/or safes, timers which prevent the opening of drawers, doors, cabinets, and/or safes for a predetermined time period, sprinkler systems, and/or notifying law enforcement or other security personnel. FIG. 7 shows an example embodiment utilizing several optional additional security measures. As shown in FIG. 7, when the activation button sends 510 a signal, this may result in deploying 520 a barrier, activating 530 cameras, engaging 540 additional security measures, and/or notifying 550 security personnel or law enforcement. If cameras are activated 530, the cameras may start recording 533 visual data, focusing 535 on the service personnel area, and/or maintaining 537 recordings that may have been deleted or otherwise lost. If the system engages 540 additional security measures, this may include activating 541 a security alarm, activating 542 sirens, activating 543 flashing lights, activating 544 locks, activating 545 timers and/or activating 546 a dye mechanism.

Figure 8A:
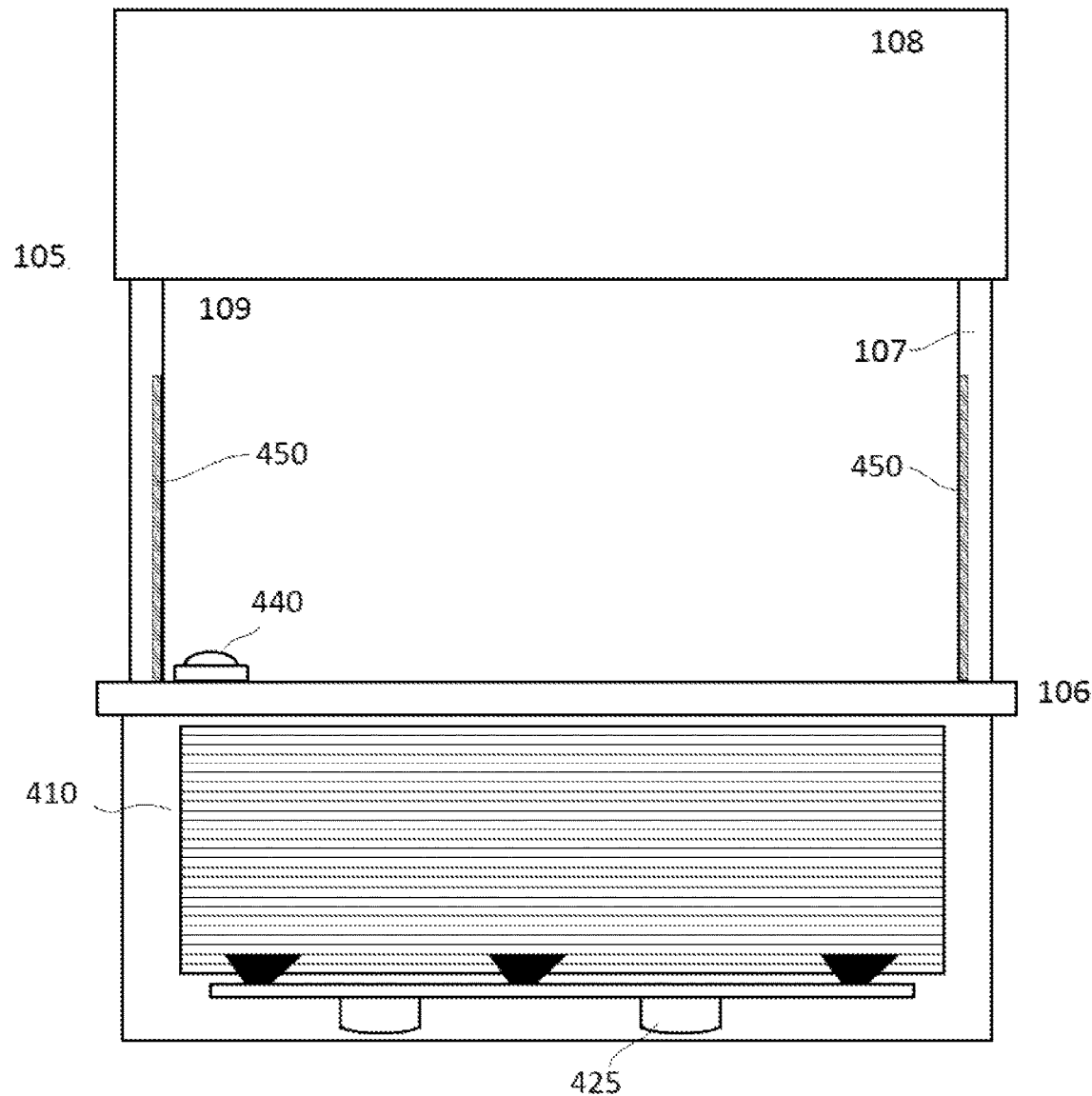
FIG. 8A illustrates a service personnel booth equipped with a deployable shield in the stored position according to an example embodiment.
Figure 8B:
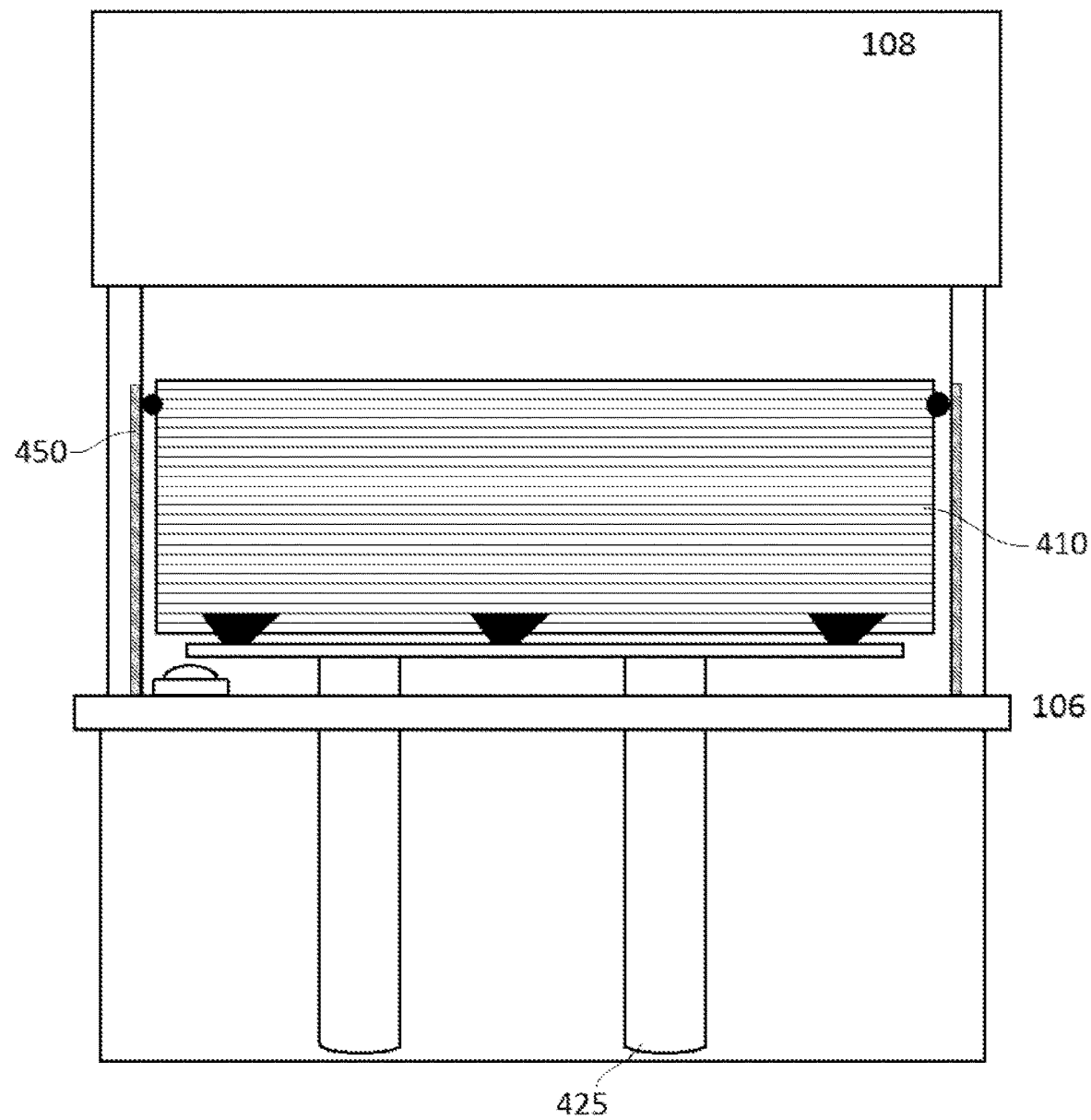
FIG. 8B illustrates a service personnel booth equipped with a deployable shield in the deployed position according to an example embodiment.

As shown in FIGS. 8A-B, certain disclosed embodiments relate to a service personnel booth 105 which includes a structure consisting of a counter or desk surface 106, at least two vertical members 107 and an upper cross member 108. These structural components collectively define the service personnel window 109. In these embodiments, a shield 410 may be attached to an actuator 425 such that the actuator 425 moves the shield 410 from a stored position to a deployed position. The service personnel booth 105 may also have a guide rail 450 secured to the structure, wherein the guide rail 450 can be designed to guide and/or facilitate the movement of the shield 410 from the stored position to the deployed position. The service personnel booth 105 may also include an initiation button 440 which can be connected to the actuator 425, such that pressing the initiation button 440 generates a signal which causes the actuator 425 to move the shield 410 from the stored position to the deployed position. The shield 410 may be stored anywhere within the disclosed service personnel booth 105 including underneath the counter surface 106 or above the window 109 concealed within the upper cross member 108.

Figure 9A:
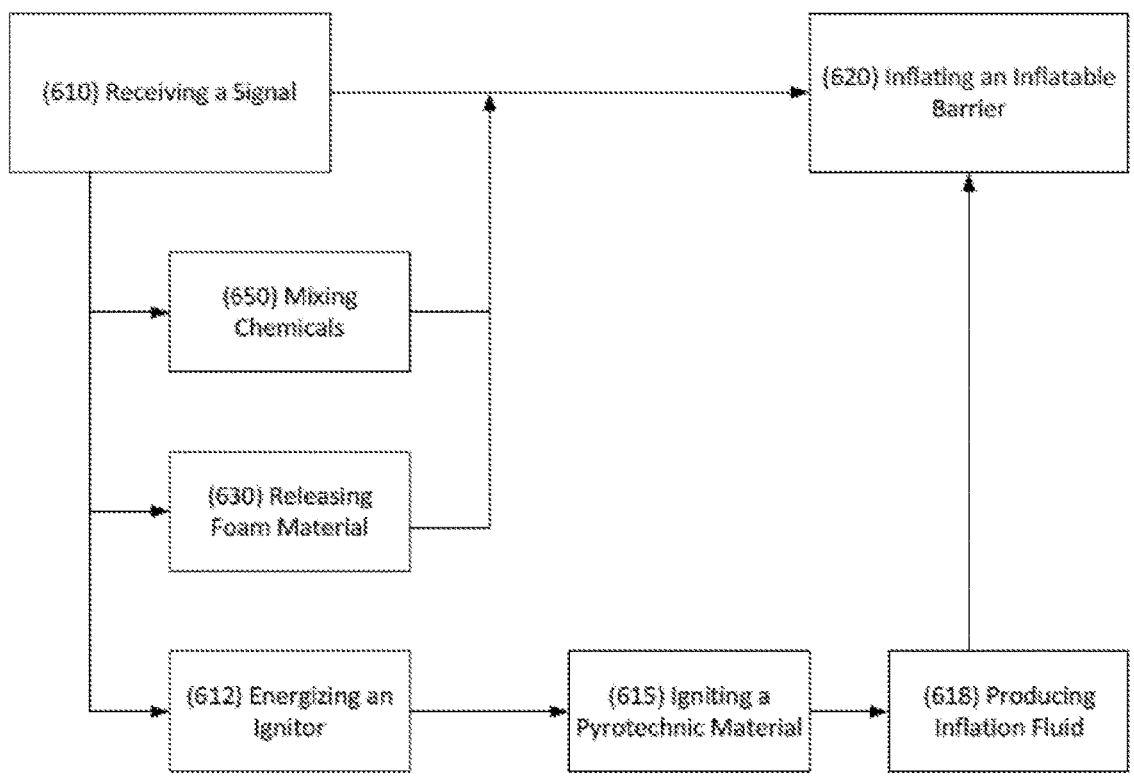
FIG. 9A illustrates a disclosed method of protecting service personnel using a security system according to an example embodiment.

Example embodiments of a method for protecting service personnel are also disclosed. As shown in FIG. 9A, the embodiments of the disclosed method may include the steps of, upon receiving 610 a signal from an activation button, inflating 620 a flexible barrier using an inflation fluid source, wherein the flexible barrier comprises bullet resistant material. In some embodiments, the method may also include the steps energizing 612 an ignitor, igniting 615 a pyrotechnic material using an electrically energizable ignitor upon receiving a signal from the activation button, and producing 618 an inflation fluid. Certain embodiments may also include the steps of releasing 630 an expandable foam material from a container upon receiving a signal from the activation button, or mixing 650 a first chemical component and a second chemical component in order to form an expandable foam.

Figure 9B:
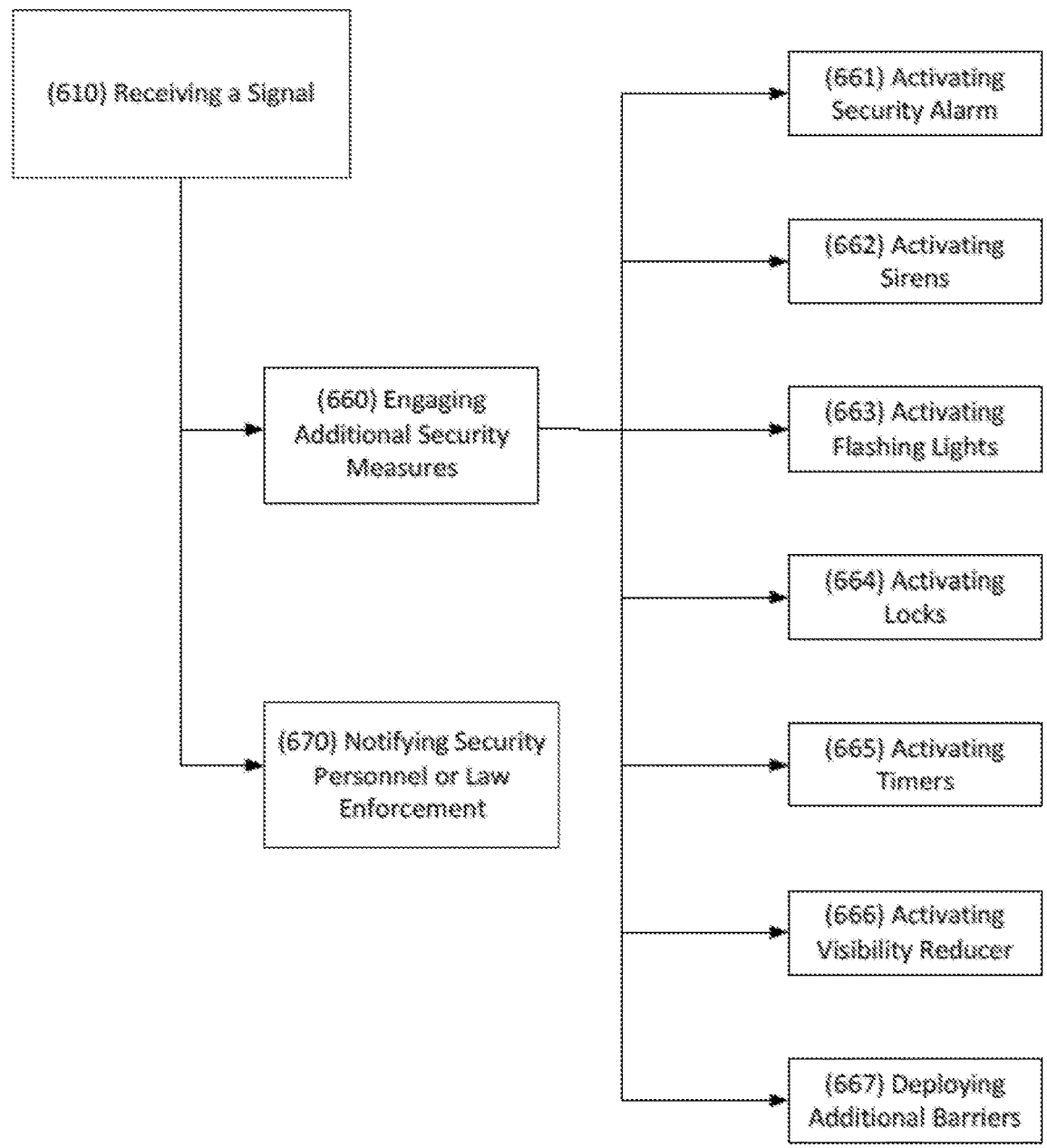
FIG. 9B illustrates additional security measures for protecting service personnel following the method illustrated in FIG. 9A according to an example embodiment.

As shown in FIG. 9B, additional method steps may include engaging 660 additional security measures including, but not limited to, activating 661 a security alarm, activating 662 sirens, activating 663 flashing lights, activating 664 electronic locks, and/or activating 665 a timer, wherein the timer prevents the opening of a safe, exterior doors, and/or interior doors for a predetermined period of time. Some embodiments include the step of, upon receiving a signal from the activation button, notifying 670 a local police department or other law enforcement organization. Some embodiments may additionally or alternative, include the additional security measures of activating 666 a smoke bomb, fog machine, flash grenade or other visibility reducing device upon receiving a signal from the activation button. Some embodiments may also include the additional security measure of inflating or otherwise deploying 667 additional barriers upon receiving a signal from an activation button.

Many disclosed embodiments generally relate to a system for protecting personnel including a bullet resistant panel; a deployment mechanism including an actuation cylinder and a source of pressurized fluid, wherein the actuation cylinder is operably connected to a bullet resistant panel; and an activation switch operably connected to the deployment mechanism, wherein the deployment mechanism is configured to move the bullet resistant panel from a stored position to a deployed position upon receiving a signal from the activation switch. Embodiments may also include a guide track for guiding the movement of the bullet resistant panel, wherein at least a portion of the bullet resistant panel is movably connected to the guide track; an alarm operably connected to the activation switch, wherein the alarm is configured to alert security personnel upon receiving a signal from the activation switch; and/or a second bullet resistant panel, wherein the deployment mechanism is configured to move the bullet resistant panels in substantially opposite directions and/or wherein the deployment mechanism is configured to move the bullet resistant panels substantially simultaneously. Embodiments may also include a camera system operably connected to the activation switch, wherein the camera is configured to record visual data upon receiving a signal from the activation switch; a dye mechanism operably connected to the activation switch, wherein the dye mechanism is configured to project dye in front of the bullet resistant panel upon receiving a signal from the activation switch; and/or at least one additional security device selected from the group consisting of flashers, sirens, alarms, cameras, telephonic notification devices, electronic notification devices, locks, timers, sprinkler systems, wherein the at least one additional security device is operably connected to the activation switch.

In some embodiments, the bullet resistant panel is angled at least about fifteen degrees from vertical when in the deployed position and/or the bullet resistant panel further comprises a bumper formed of a flexible material.

In still more embodiments, the activation switch is configured to require a two-finger press in order to generate a signal and/or the activation switch comprises two buttons, wherein the activation switch is configured to require both buttons to be pressed substantially simultaneously in order to generate a signal.

Some disclosed embodiments relate to a method for protecting service personnel comprising the steps of, upon receiving a signal from an activation button, inflating a flexible barrier using an inflation fluid source, wherein the flexible barrier comprises bullet resistant material. Certain embodiment also include the steps of igniting a pyrotechnic material using an electrically energizable ignitor upon receiving a signal from the activation button and producing an inflation fluid; releasing an expandable foam material from a container upon receiving a signal from the activation button; mixing a first chemical component and a second chemical component in order to form an expandable foam; notifying a local police department; activating an electronic locking mechanism; and/or activating a timer, wherein the timer prevents the opening of a safe for a predetermined period of time.

Additional disclosed embodiments relate to a service personnel booth comprising a structure wherein the structure comprises a counter surface, a first vertical member, a second vertical member, and an upper cross member which collectively define a window space; a shield comprising bullet resistant material; an actuator configured to move the shield from a stored position to a deployed position; a guide rail configured to guide the movement of the shield when the shield is moved from the stored position to the deployed position and wherein the guide rail is secured to the structure; and an initiation button, wherein the initiation button is operably connected to the actuator, and wherein the actuator is configured to move the shield from the stored position to the deployed position upon receiving a signal from the initiation button.

The present disclosure is not to be limited in terms of the particular embodiments described in this application, which are intended as illustrations of various aspects. Many modifications and variations can be made without departing from its spirit and scope, as may be apparent. Functionally equivalent methods and apparatuses within the scope of the disclosure, in addition to those enumerated herein, may be apparent from the foregoing representative descriptions. Such modifications and variations are intended to fall within the scope of the appended representative claims. The present disclosure is to be limited only by the terms of the appended representative claims, along with the full scope of equivalents to which such representative claims are entitled. It is also to be understood that the terminology used herein is for the purpose of describing particular embodiments only, and is not intended to be limiting.

What is claimed is:

1. An inflation barrier, comprising:
 a self-healing liner, wherein the self-healing liner is configured to:
  receive an inflation fluid from an inflation fluid source, and
  substantially seal an opening of the inflation barrier,
 wherein the inflation fluid source contains one or more chemical materials which generate the inflation fluid when reacted with at least one selected from the group of heat, electricity, and oxygen.

2. The inflation barrier of claim 1, wherein the inflation fluid comprising at least one selected from the group of an expandable foam and an expandable polymer.

3. The inflation barrier of claim 2, wherein:
 the inflation fluid comprises the expandable foam, and
 the expandable foam is formed by mixing a first chemical material and a second chemical material.

4. The inflation barrier of claim 1, wherein the inflation fluid source comprises an energizable ignitor.

5. The inflation barrier of claim 4, wherein the energizable ignitor is configured to ignite a pyrotechnic material upon receipt of a signal from an activation switch.

6. The inflation barrier of claim 5, wherein the ignition of the pyrotechnic material provides heat for reaction with the inflation fluid.

7. The inflation barrier of claim 5, wherein the ignition of the pyrotechnic material directs the inflation fluid into the self-healing liner.

8. The inflation barrier of claim 1, wherein the inflation fluid further comprises a filler material.

9. The inflation barrier of claim 8, wherein the filler material comprises a plurality of geometric shapes configured to dissipate force.

10. The inflation barrier of claim 1, wherein the self-healing liner contains impact absorbing particles.

11. The inflation barrier of claim 10, wherein the impact absorbing particles are configured to collapse and fill the opening.

12. A method, comprising:
 providing an inflation barrier comprising a self-healing liner configured to receive an inflation fluid and substantially seal an opening of the inflation barrier, wherein the inflation fluid source contains one or more chemical materials which generate the inflation fluid when reacted with at least one selected from the group of heat, electricity, and oxygen;
 receiving, by an inflation fluid source configured to inject the inflation fluid into the inflation barrier, a signal from an activation switch; and
 injecting, by the inflation fluid source responsive to the signal, the inflation fluid into the inflation barrier.

13. The method of claim 12, wherein injecting, by the inflation fluid source, the inflation fluid into the inflation barrier comprises reacting the one or more chemical materials with at least one selected from the group of heat, electricity, and oxygen.

14. The method of claim 12, wherein:
the inflation fluid source comprises an energizable ignitor, and
the method further comprises injecting, by the inflation fluid source, the inflation fluid into the inflation barrier comprises igniting a pyrotechnic material to generate the inflation fluid and direct the inflation fluid into the inflation barrier.

15. A system, comprising:
an inflation barrier comprising:
  a self-healing liner configured to receive an inflation fluid, and
  substantially seal an opening of the inflation barrier,
wherein the inflation fluid source contains one or more chemical materials which generate the inflation fluid when reacted with at least one selected from the group of heat, electricity, and oxygen.

16. The system of claim 15, further comprising:
an inflation fluid source configured to inject the inflation fluid into the inflation barrier; and
an activation switch operably connected to the inflation fluid source,
wherein the inflation fluid source is configured to, upon receiving a signal from the activation switch, inflate the inflation barrier by injecting the inflation fluid into the self-healing liner.

17. The system of claim 16, wherein the activation switch is configured to require a two-finger press to generate the signal.

18. The system of claim 16, wherein:
the activation switch comprises two buttons, and
the activation switch is configured to require both buttons to be pressed substantially simultaneously to generate the signal.

19. The system of claim 15, further comprising:
a panel comprising a ridged shell and a self-healing volume; and
a panel deployment mechanism operably connected to the activation switch,
wherein the panel deployment mechanism is configured to, upon receiving a signal from the activation switch, move the panel from a stored position to a deployed position.

20. The system of claim 19, wherein:
the self-healing volume contains an inner lining enclosing a filler material and a plurality of force dissipation shapes, and
the inner lining comprises an elastomer and is configured to substantially close around a damaged area of the panel.

* * * * *